United States Patent [19]

Hrebeniuk

[11] Patent Number: Plant 6,890

[45] Date of Patent: Jun. 27, 1989

[54] POINTSETTIA PLANT NAMED H-524

[76] Inventor: Alexander Hrebeniuk, R.D. #1, Box 118, Sugar Run, Pa. 18846

[21] Appl. No.: 159,955

[22] Filed: Feb. 24, 1988

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Poinsettia plant named H-524, characterized by its light yellow bract color, early flower response, large bract size, compact growth habit, and its ability to perform well pinched or unpinched in 3½" to 12" pot programs.

1 Drawing Sheet

The present invention relates to a new and distinct cultivar of Poinsettia plant know by the cultivar name H-524, and botanically known as *Euphorbia pulcherrima.*

H-524 is a product of a planned breeding program which had the objective of creating new Poinsettia cultivars with yellow bract color, early flower response, compact growth habit, and large bract development. Such traits in combination were not present or needed improvement in previously available commercial cultivars.

H-524 was originated from a hybridization made by applicant in a controlled breeding program in Sugar Run, Pa. in 1985. The female parent was C-1 White, disclosed in U.S. Plant Pat. No. 3,196. The male parent of H-524 was V-14 Glory, disclosed in U.S. Plant Pat. No. 4,384. H-524 was discovered and selected as one flowing plant within the progeny of the stated parentage by applicant in January 1986 in a controlled environment in Sugar Run, Pa.

The first act of sexual reproduction of H-524 was accomplished when vegatative cuttings were taken from the initial selection in April, 1986 in a controlled environment in Sugar Run, Pa. by a technician working under formulations established and supervised by applicant. Horticultural examination of selected units initiated in December 1986 has demonstrated that the combination of characteristics as herein disclosed for H-524 are firmly fixed and are retained through successive generations of asexual reproduction.

H-524 has not been observed under all possible environmental conditions. The phenotype may vary significantly with variations in environment such as temperature, light intensity, and day length. The following observations, measurements and comparisons describe plants grown in Sugar Run, Pa. under greenhouse conditions which approximate those generally used in commercial practice.

The following traits have been repeatedly observed and are determined to be basic characteristics of H-524 which in combination distinguish this Poinsettia as a new and distinct cultivar:

1. Light yellow bract color.
2. Early 8.5 week flower response.
3. Large bract size.
4. Excellent shipping and keeping quality; cyathia are persistent.
5. Compact growth habit.
6. Displays botrytis resistance.

7. Performs well pinched or unpinched in 3½" to 12" pot programs.
8. Requires 66°-68° F. nights and 75° F. days for best bract development. After November 15, night temperatures can be dropped to 62° F.

The accompanying photographic drawing shows typical inflorescence and foliage characteristics of H-524, with colors being as nearly true as possible with illustrations of this type. The photograph is in black and white, with one leaf, several bracts, and cyathia being colored to accurately depict true color.

In the following description color references are made to The Royal Horticultural Society Colour Chart. The color values were determined between 2:00 and 2:30 p.m. on Dec. 18, 1987 under florescent light at Parrish, Fla.

Classification:
- *Botanical.*—Euphorbia pulcherrima.
- *Commercial.*—Poinsettia.

Parentage:
- *Male parent.*—V-14.
- *Female parent.*—C-1 White.

Plant description:
- (A) *Form.*—Triple.
- (B) *Growth habit.*—Upright and compact.
- (C) *Rooting.*—Fast, with few problems.
- (D) *Blooming season.*—November 15th through December 10th.
- (E) *Blooming habit:* Large bracts in treble rows.

Foliage:
- (A) *Size.*—Width, 7-12 cm. Length, 10-15 cm.
- (B) *Quality.*—Up to 20 leaves per flowering stem.
- (C) *Color.*—New foliage: Upper side: 137A. Under side: 137C. Old foliage: Upper side: 147A. Under side: 137A. Leaf petiole: 145A.
- (D) *Shape.*—Ovate, apex acuminate, margins variable, ranging from repand to sinuate, some leaves display two or four marginal teeth.
- (E) *Texture.*—Upper side: velvety. Under side: veins prominent, velvety between them.
- (F) *Edge of margin.*—Slightly wavy to slightly pointed.
- (G) *Aspect.*—Pointed.
- (H) *Disease resistance.*—Very resistant to botrytis.

Flowers:
- (A) *Borne.*—In a compound corymb.
- (B) *Quantity.*—16 to 22 cyathia per stem, each flower having a nectary.

Bracts:

(A) *Size.*—From 1 cm wide to 2.5 cm long, and up to 14 cm wide by 17 cm long on a plant grown unpinched.

(B) *Color.*—5D.

Reproductive organs: Typical Poinsettia, insignificant.

I claim:

1. A new and distinct cultivar of Poinsettia plant named H-524, as described and illustrated, and parts thereof.

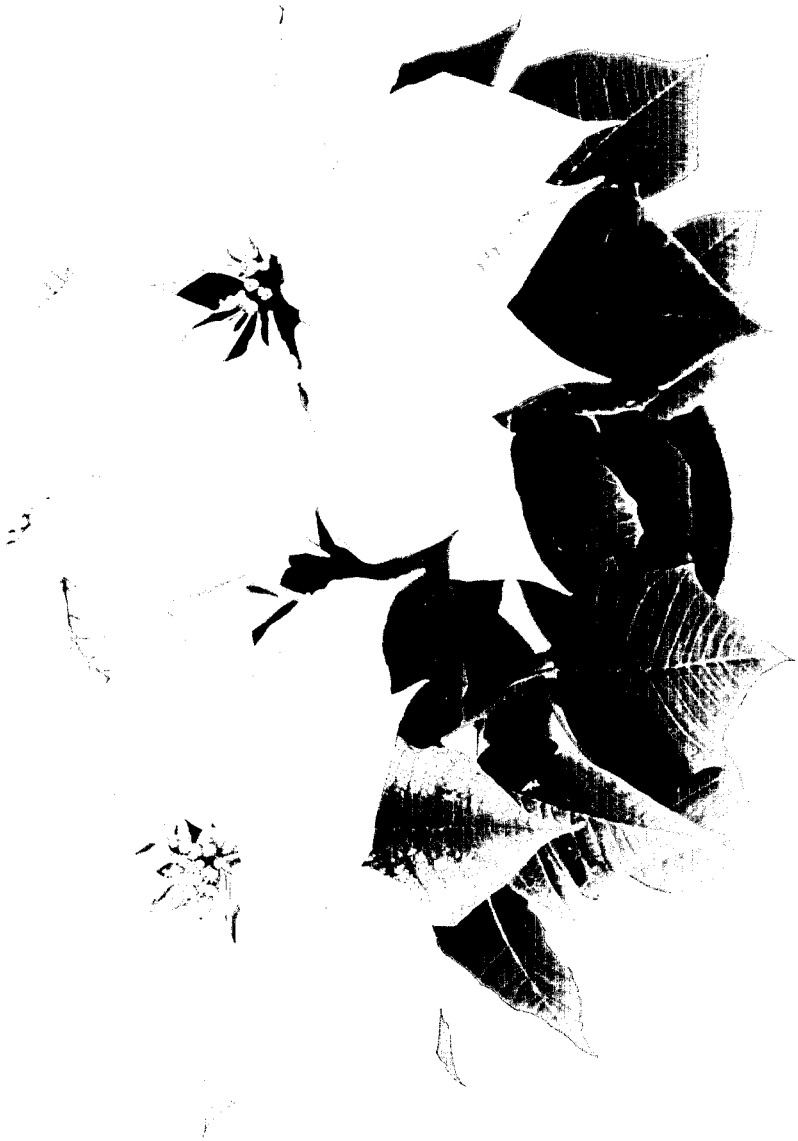

* * * * *